United States Patent
Akiba (10) Patent No.: US 6,595,915 B2
(45) Date of Patent: Jul. 22, 2003

(54) JET NOZZLE FOR WASHING OBSERVATION WINDOW OF ENDOSCOPIC INSERTION INSTRUMENT

(75) Inventor: Haruo Akiba, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/908,577

(22) Filed: Jul. 20, 2001

(65) Prior Publication Data

US 2002/0026097 A1 Feb. 28, 2002

(30) Foreign Application Priority Data

Aug. 17, 2002 (JP) ......................................... 2000-247249

(51) Int. Cl.$^7$ ................................................ A61B 1/12
(52) U.S. Cl. ........................................ 600/157; 600/158
(58) Field of Search ..................................... 600/157, 158, 600/159

(56) References Cited

U.S. PATENT DOCUMENTS

| | | | | |
|---|---|---|---|---|
| 5,386,817 A | * | 2/1995 | Jones ........................ | 600/157 |
| 5,518,502 A | * | 5/1996 | Kaplan et al. ............... | 600/157 |
| 5,685,823 A | * | 11/1997 | Ito et al. ..................... | 600/157 |
| 5,725,476 A | * | 3/1998 | Yasui et al. ................. | 600/157 |
| 6,409,657 B1 | * | 6/2002 | Kawano ..................... | 600/158 |

* cited by examiner

*Primary Examiner*—Linda C. M. Dvorak
*Assistant Examiner*—Jocelyn Ram
(74) *Attorney, Agent, or Firm*—Oblon, Spivak, McClelland, Maier & Neustadt, P.C.

(57) ABSTRACT

A jet nozzle for spurting a wash fluid toward an observation window of an optical image pickup system fitted in a rigid tip end section of the insertion instrument for cleaning the observation window. The jet nozzle includes an inlet passage portion which is provided at a proximal end of the jet nozzle coaxially in communication with an axial wash fluid passage in the rigid tip end section of the insertion instrument, a jet spout passage portion which is located on a distal end face of the rigid tip end section and terminating with a jet spout opening of a predetermined width. The jet spout passage portion is provided with a straight flow rectifying passage of a predetermined length toward the jet outlet opening. The jet nozzle further includes a turn passage portion which is connected between the wash fluid inlet passage and the jet spout passage portion to turn a flow passage of the wash fluid in a radially diverting direction from the axial wash fluid passage, and connected to the jet spout passage portion in a radially diverted position on the distal end face of the rigid tip end section.

6 Claims, 9 Drawing Sheets

JET NOZZLE FOR WASHING OBSERVATION WINDOW OF ENDOSCOPIC INSERTION INSTRUMENT

BACKGROUND OF THE INVENTION

1. Field of the Art

This invention relates to an endoscopic insertion instrument for medical use, and more particularly to a jet nozzle to be connected to a wash fluid feed passage for washing an observation window on a distal end face of the insertion instrument.

2. Prior Art

Figure 8:
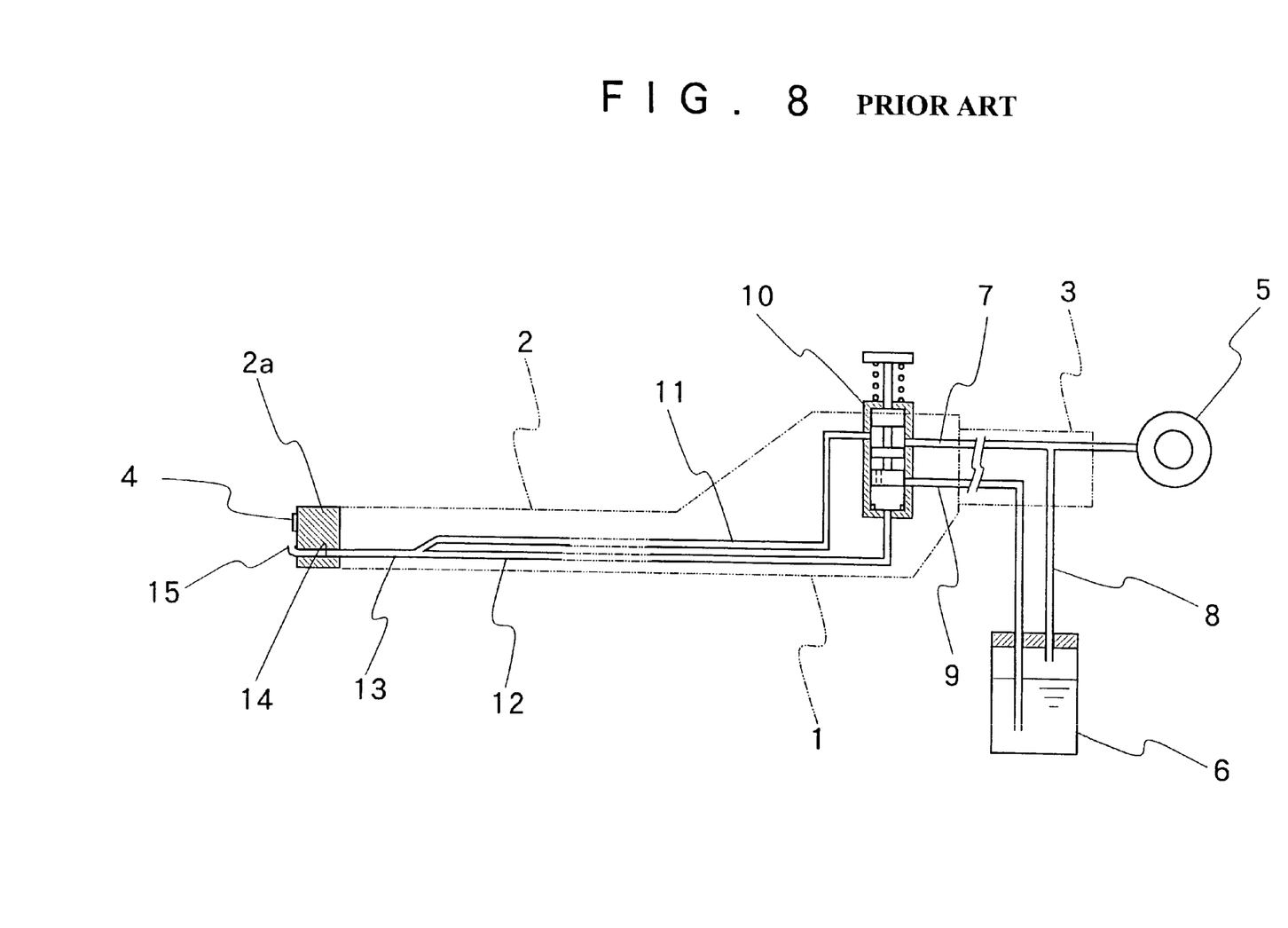
FIG. 8 is a schematic illustration of a washing device which is in general use for washing an observation window of an endoscope.

Illustrated in FIG. 8 is a typical endoscope in general use in medical fields. In that figure, indicated at 1 is a manipulating head assembly, at 2 an insertion instrument, and at 3 a universal cable. Along with an illumination window or windows, an observation window 4 is provided on a rigid tip end section 2a of the insertion instrument 2. An optical objective lens system is disposed on the inner side of the observation window 4, and an image sensor device such as a solid-state image sensor or the like is located at the focus of the optical objective lens system. Fitted in the observation window 4 is a cover glass which also functions as a foremost lens element of the objective lens system. When the endoscopic insertion instrument 2 is introduced into a body cavity of a patient, it is very likely for the surface of the foremost lens element to be smeared by deposition of body fluids or other contaminants. Deposition of such contaminants on the lens surface results in restrictions of the view field and therefore in insufficient examination of an intracavitary portion under observation.

Thus, a device for washing an endoscopic observation window is necessary for washing the exterior surface of the observation window and removing contaminants therefrom whenever a view through the observation window 4 is smeared by deposition of contaminants during examination of a body cavity. For washing the observation window 4, wash water is spurted toward the lens surface under a predetermined pressure to wash away contaminants, and then compressed air is blasted on the lens surface to purge water droplets.

For these purposes, the observation window washing device is equipped with an air pump 5 and a water tank 6. A compressed air pipe 7 from the air pump 5 is connected to the universal cable 3. Further, a tank pressurizing air pipe 8 is branched off the compressed air pipe 7, and connected to the water tank 6 which receives a supply of water through a wash water feed pipe 9. In this instance, the tank pressurizing air pipe 8 is opened above the surface of water in the tank 6, while the wash water feed pipe 9 is opened under the water surface, preferably in the vicinity of the bottom of the water tank 6. Compressed air pipe 7 and the water pipe 9 are extended into the manipulating head assembly 1 by way of the universal cable 3 and connected to a air/water feed valve 10 which is provided on the manipulating head assembly 1.

Connected from the air/water feed valve 10 are an air feed pipe 11 and a water feed pipe 12, which are jointed together in a fore end portion of the insertion instrument 2 into an air/water junction pipe 13. The air/water junction pipe 13 is communicated with a fluid passage 14 which is bored in the rigid tip end section 2a. The fluid passage 14 is opened in a distal end face of the rigid tip end section 2a, and provided with a spout nozzle 15 at its open end. A wash fluid, consisting of water and compressed air flowing through the fluid passage 14, is turned and spurted toward the observation window 4 by the spout nozzle 15 under a predetermined pressure. Therefore, the spout nozzle 15 is provided with a mouth end which is turned toward the observation window 4.

The air/water feed valve 10 can be manipulated by a finger of a hand which grips the manipulating head assembly 1. Normally, communication between the wash water pipe 9 and the water feed pipe 12 is blocked, while the compressed air pipe 7 is connected to the air feed pipe 11 and at same time communicated with the atmosphere through an atmospheric passage (not shown) which is provided in the air/water feed valve 10. Thus, at this time, the air/water feed is in a suspended state. Since the compressed air pipe 7 is in communication with the atmosphere, the pump 5 is substantially in an unloaded state. As soon as the atmospheric passage is blocked by a finger or the like, the air pump 5 turns into a loaded state and starts to compress air. Resulting compressed air is supplied to the jet nozzle 15 from the compressed air pipe 7 through the air feed pipe 11 and the compressed air pipe 8. At the same time, the air pressure is led into the wash water tank 6 through the compressed air pipe 8 to pressurize the wash water tank 6. However, no wash water is supplied to the jet nozzle 15 because the communication between the wash water pipe 9 and the water feed pipe 12 is still blocked by the air/water feed valve 10.

Upon pushing in the air/water feed valve 10 from the position shown in the drawing, communication between the compressed air pipe 7 and the air feed pipe 11 is blocked while communication between the wash water pipe 9 and the water feed pipe 12 is opened. Further, compressed air from the air pump 5 is introduced into the wash water tank 6 through the tank pressurizing pipe 8 to pressurize the wash water tank 8, whereupon wash water is supplied to the fluid passage 14 under a predetermined pressure through the wash water pipe 9 and the water feed pipe 12. As a result, wash water is spurted toward the observation window 4 from the jet nozzle 15.

Figure 9:
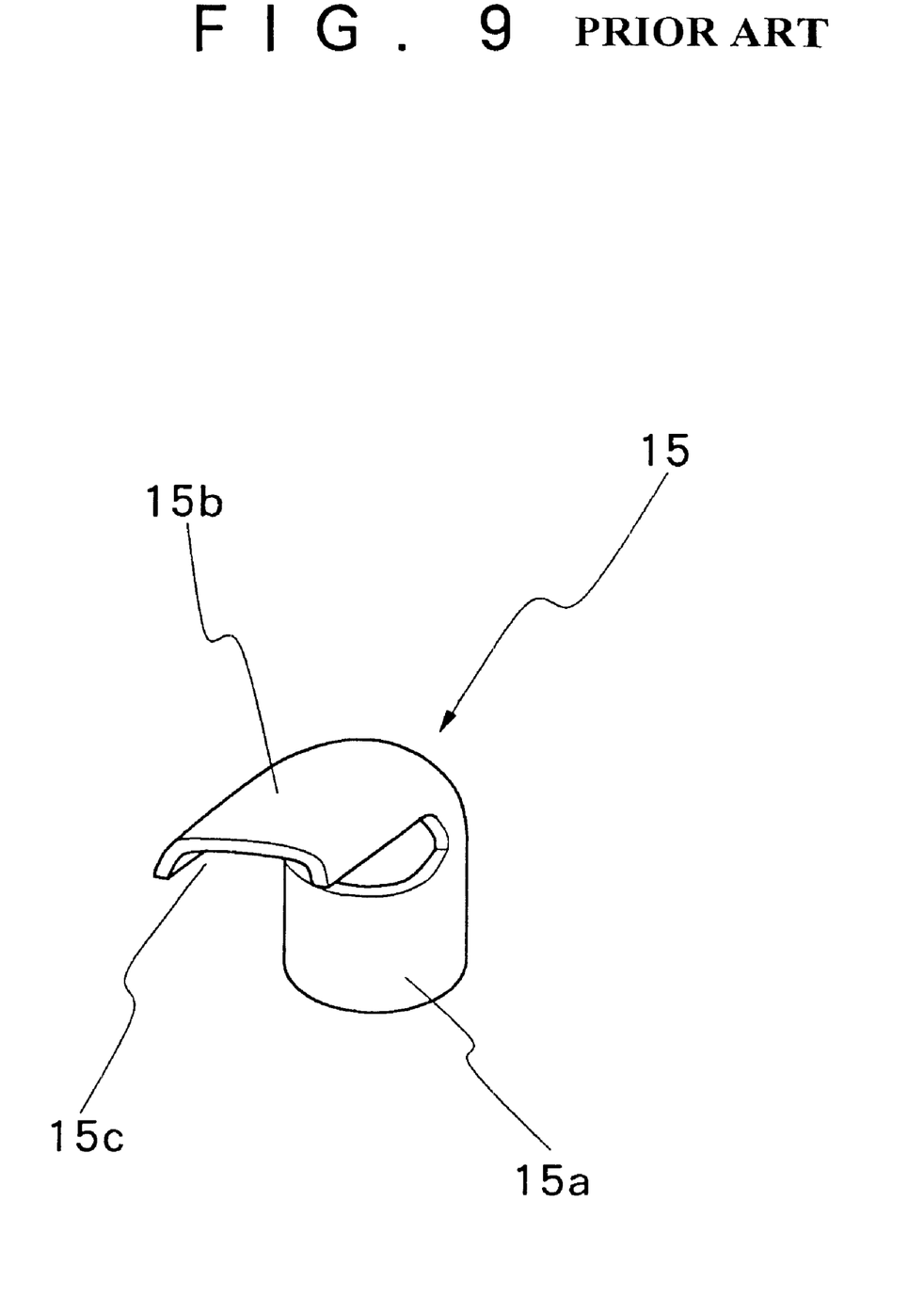
FIG. 9 is a schematic perspective view of a prior art jet nozzle.

As shown in FIG. 9, the prior art jet nozzle 15 is constituted, for example, by a tubular body portion 15a, and a jet spout passage portion 15b which is turned approximately through 90 degrees from the tubular body portion 15a and terminated with an injecting nozzle hole 15c at its fore distal end. In this instance, the jet spout passage portion 15b is a flat passage. The passage of the jet spout passage portion can be formed simply by bending an intermediate portion of the tubular body portion 15a through 90 degrees in a flattened shape. However, in the case of the particular example shown, a lower side portion of the jet spout passage portion 15 is removed to spurt a fluid toward the surface of the rigid tip end section 2a.

A wash fluid including wash water and/or compressed air, which is spurted out through the nozzle hole 15c of the jet nozzle 15, should be precisely directed toward and distributed over the entire surfaces of the observation window 4. In addition, a wall portion of the jet nozzle 15 should not block a view field through the observation window 4. In order to fulfill these requirements, the nozzle hole 15c needs to be located at a certain distance from the observation window 4. Accordingly, position of the jet nozzle 15 and direction of the jet spout passage portion 15b on the rigid tip end section 2a of the insertion instrument 2 are determined depending upon the position of the observation window 4 itself. Besides, the jet nozzle 15 is also restricted by the position of an illumination window or windows. In a case where the jet nozzle 15 is located in the proximity of an illumination window, it is likely that illumination light is reflected off the jet nozzle and directed toward the observation window 4 as harmful light to endoscopic observation images. Therefore, the jet nozzle 15 should be located at a distance from an illumination window. Of course, the position of an illumination window is determined depending upon the position of the observation window 4. Namely, in order to distribute illumination light uniformly over the entire view field which is obtained through the observation window 4, illumination windows need to be located in positions on the right and left sides and in the proximity of the observation window 4.

The position of the observation window 4 on the rigid tip end section 2a of the insertion instrument 2 is limited by relations with its view field. More specifically, normally the proximal end of the rigid tip end section 2a is connected to an angle section which is flexibly and angularly bent in an upward, downward, rightward or leftward direction to turn the rigid tip end section 2a into a desired direction. Therefore, the bending direction and the position of the observation window 4 are in certain relations with each other. The observation window 4 is located either in a center position or in an off-center position on the distal end face of the rigid tip end section 2a. In case the observation window 4 is located in an off-center position, an operator can manipulate and control the insertion instrument more easily if the observation window 4 is located in an upper position in the bending direction of the angle section. Further, the position of an outlet opening of a biopsy channel, which is provided in the insertion instrument 2 for passing forceps or other biopsy or surgical instruments, is also closely related with the position of the observation window 4. Namely, as a biopsy instrument is protruded into a body cavity from the outlet opening of the biopsy channel, it should always be within the view field of the observation window 4. Besides, the an extension of the outlet opening of the biopsy channel should not intersect a direction of fluid injection by the jet nozzle 15. In short, once the observation window 4 is located in a certain position on the rigid tip end section 2a of the insertion instrument 2, the positions of the illumination windows, outlet opening of the biopsy channel and jet nozzle 15 are determined accordingly.

After setting the jet nozzle 15 in a position which satisfies the conditions as discussed above, the position of the fluid passage 14 in the rigid tip end section 2a is determined accordingly. The fluid passage 14 is connected to the air/water junction pipe 13 in the flexible angle section which is connected to the proximal end of rigid tip end section 2a. The air/water junction pipe 13 in the angle section has to be constituted by a soft, flexible tube with a wall thickness which is sufficient to ensure immunity from buckling even when the insertion instrument 2 is bent into angular forms. For this purpose, the junction pipe 13 which is extended from the rigid tip end section 2a has to be relatively large in outside diameter. In addition, a lead portion of the junction pipe 13 has to be located in such a way as to avoid interference with various component parts such as light guide, signal cable and biopsy channel which are are fitted in or threaded through the angle section of the insertion instrument 2, on the proximal side of the rigid tip end section 2a.

Further, in a case where the optical objective lens system is arranged to move part of its lens components in the direction of optical axis for a zooming action, for example, it is necessary to incorporate a mechanism for axially displacing a movable lens or lenses by remote control. In this regard, it has been the general practice to move movable lenses by mean of a control cable having tightly closed rotation transmission coils sheathed in a flexible sleeve. The junction pipe should be located in such a position which would not interfere with a control cable when the latter is fitted into the insertion instrument 2. Thus, the provision of a control cable, in addition to the above described various internally fitted component parts which are interdependent on each other in positional layout, necessarily results in a conspicuous increase in diameter of the endoscopic insertion instrument 2.

SUMMARY OF THE INVENTION

With the foregoing situations in view, it is an object of the present invention to reduce the diameter of an endoscopic insertion instrument by minimizing dead spaces in the insertion instrument in connecting a fluid passage to a rigid tip end section of the insertion instrument.

It is another object of the present invention to provide a jet nozzle which spurts jets of a wash fluid toward an observation window of an endoscopic insertion instrument, which give a greater freedom in locating a wash fluid passage in a fore end portion of the insertion instrument, allowing to lay out other internally fitted component parts of the insertion instrument in a rational way.

It is still another object of the present invention to provide a jet nozzle of the sort as mentioned above, which can suppress increases in diameter of an endoscopic insertion instrument to a minimum by making it possible to locate a wash fluid passage in a suitable position, particularly in a case where a control cable is additionally fitted into the insertion instrument for the purpose of driving a movable lens or lenses of an optical objective lens system.

In accordance with the present invention, for achieving the above-stated objectives, there is provided a jet nozzle to be connected to a distal end of a wash fluid passage in a narrow and elongated endoscopic insertion instrument for spurting a wash fluid toward and on an observation window of an optical image pickup system fitted in a rigid tip end section of the insertion instrument. The jet nozzle according to the present invention is characterized by the provision of: a wash fluid inlet passage provided at a proximal end of the jet nozzle coaxially in communication with an axial wash fluid passage in the rigid tip end section of the insertion instrument; a jet spout passage portion located on a distal end face of the rigid tip end section and terminating with a jet spout opening of a predetermined width, the jet spout passage portion being provided with a straight flow rectifying passage of a predetermined length to the jet outlet opening; and a turn passage connected between the wash fluid inlet passage and the jet spout passage portion to turn a flow passage of the wash fluid in a radially diverting direction from the axial wash fluid passage and connected to the jet spout passage portion in a radially diverted position on the distal end face of the rigid tip end section.

In this instance, the flow rectifying passage of the jet spout passage portion of the jet nozzle is in the form of either a straight passage or a forwardly diverging passage having a predetermined width. The turn passage of the jet nozzle is bent in a curved shape to switch the flow direction of the wash fluid and connected to the flow rectifying passage in a radially diverted position from the axial wash fluid passage. In a case where part of lenses of the optical objective lens system are movable lenses, a lens drive means such as a control cable having tightly wound coils sheathed in a flexible sleeve is fitted into the insertion instrument to permit to move the movable lenses in the direction of optical axis by remote control. Preferably, the flow rectifying passage of the jet nozzle is located on the distal end face of the rigid tip end section at a position which is on an axial extension line from the lens drive means, while the turn passage is connected to the axial wash fluid passage which is located in an evasive position with respect to the lens drive means.

The above and other objects, features and advantages of the present invention will become apparent from the following particular description of the invention, taken in conjunction with the accompanying drawings which show by way of example preferred embodiments of the invention. Needless to say, the present invention should not be construed as being limited to particular forms shown in the drawings.

DESCRIPTION OF PREFERRED EMBODIMENTS

Shown in FIGS. 1 through 6 is a first embodiment according to the present invention. In this instance, an observation window washing device which is incorporated into an endoscopic insertion instrument is same as the above-described prior art device, except constructions and arrangements of a fluid passage and an jet nozzle on a rigid tip end section of the insertion instrument. Therefore, in the following description of the first embodiment, detailed explanations on same constituent parts of the observation window washing device are omitted to avoid repetitions of same explanations.

Figure 1:
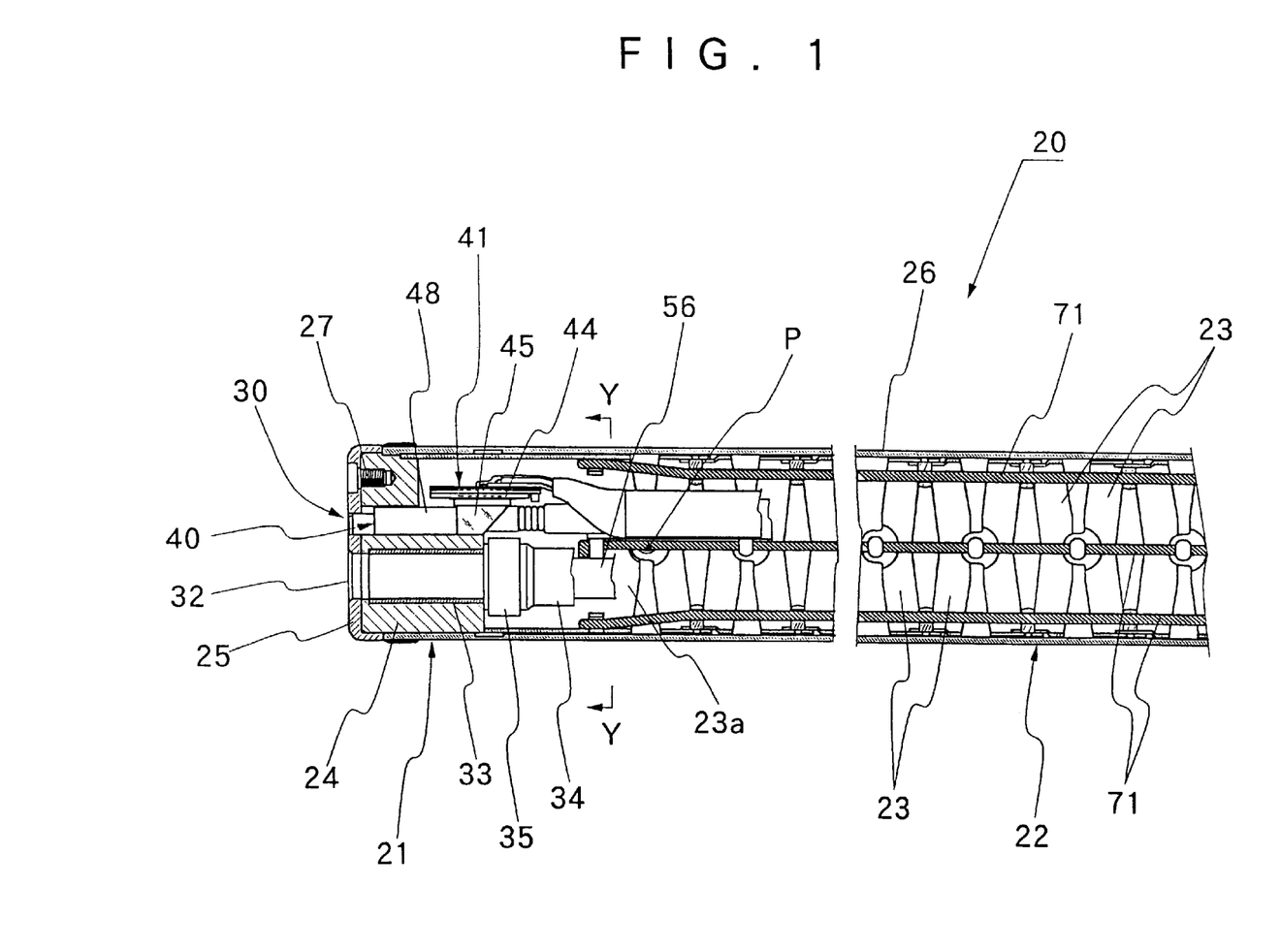
FIG. 1 is a schematic sectional view taken through a fore end portion of an endoscopic insertion instrument in one embodiment of the present invention.
Figure 2:
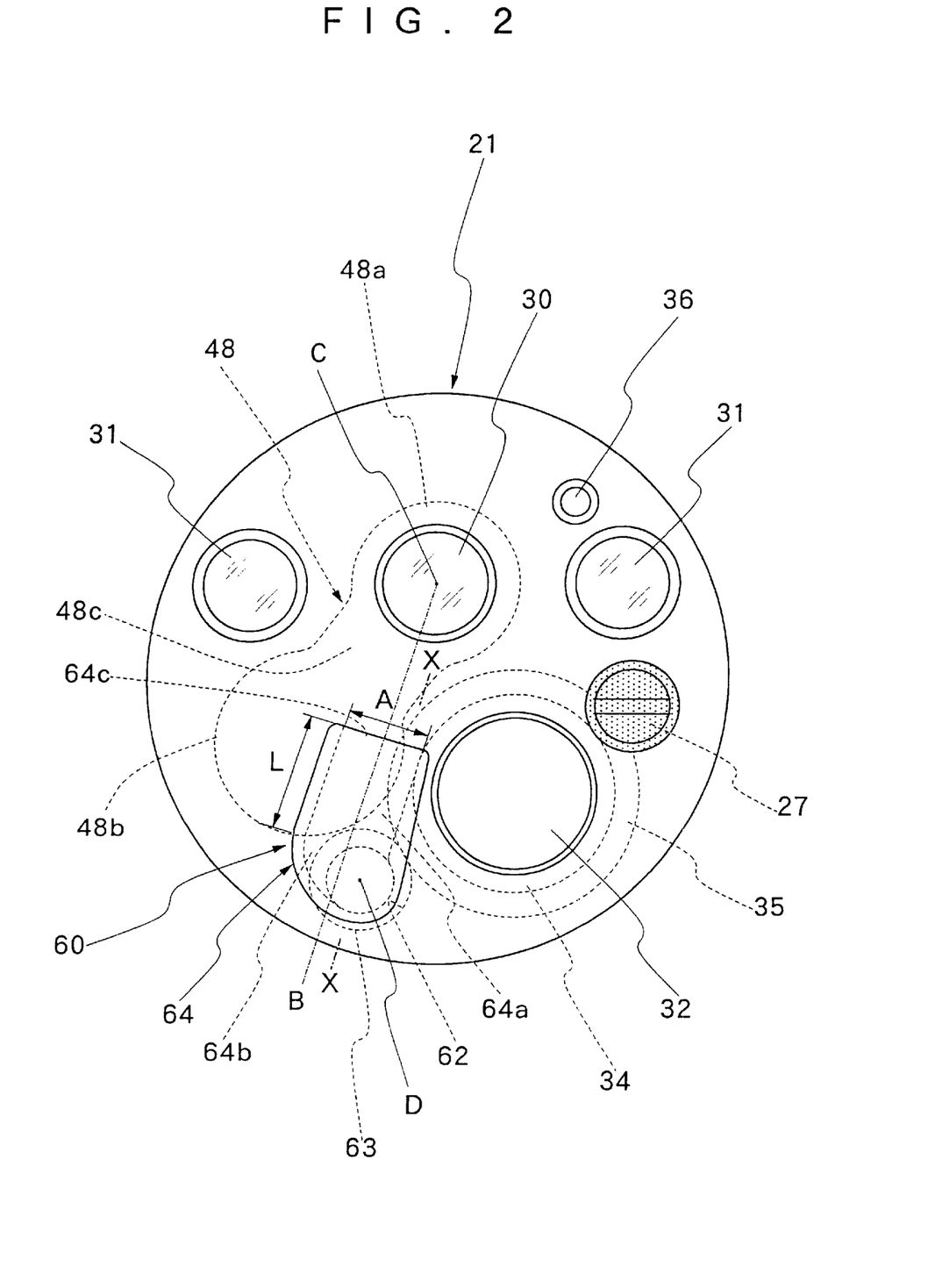
FIG. 2 is a schematic outer view of a distal end face of the insertion instrument.

Shown in FIG. 1 is a fore end portion of an elongated endoscopic insertion instrument 20, and shown in FIG. 2 is a distal end face of the insertion instrument 20. In these figures, indicated at 21 is a rigid tip end section and indicated at 22 an angle section of the insertion instrument. As well known in the art, the angle section 22 is constituted by a series of angle rings 23 which are successively pivotally connected with each other. Of the entire insertion instrument 20, a fore end portion between a fore distal end of the rigid tip end section 21 and a point of pivotal connection P of a foremost angle ring 23a with an proximally ensuing angle ring 23 is rigid, while the remaining portions on the proximal side of the rigid fore end portion are flexibly bendable substantially in arbitrary directions.

The rigid tip end section 21 is largely constituted by a tip end casing 24 and an insulating end cap 25. The tip end casing 24 is a rigid metallic structural member which imparts strength to the rigid tip end section 21. On the other hand, the insulating end cap 25 enshrouds the tip end casing 24 of metal to keep the latter in an unexposed state. Further, an outer skin layer 26 is formed around the angle section 22 in such a way as to wrap in the angle rings. The fore end of this outer skin layer 26 of the angle section 22 is abutted against a proximal end face of the insulating cap 25, and fixedly anchored in position by means of line wrapping and an adhesive. In the drawings, indicated at 27 is a stop screw which securely fixes the insulating cap 25 to the tip end casing 24. A head portion of the stop screw 27 is sunken in the insulating cap 25, and seal material is filled in a sunken hole in the insulating cap 25 to cover and keep the stop screw 27 in an unexposed state.

As seen particularly in FIG. 2, an observation window 30 is provided in the distal end face of the rigid tip end section 21, along with illumination windows 31 which are located on right and left sides of the observation window 30. Disposed in each illumination window is a light emitting end of a light guide thereby to cast illumination light toward a subject of observation within a body cavity. Further, an outlet hole 32 of a biopsy channel is opened in the distal end face of the rigid tip end section 21 to project therethrough forceps or biopsy or surgical instrument into a body cavity. This outlet hole 32 of the biopsy channel is a passage which is bored through the insulating cap 25 and the tip end casing 24. A connector pipe 33 is fitted in part of the biopsy channel outlet hole 32. In turn, fitted on the connector pipe 33 is a fore end portion of a biopsy channel 34 which is made of a flexible tube. The flexible tube of the biopsy channel 34 is securely fixed to the connector pipe 33 by means of a stopper ring 35. In this instance, the flexible tube of the biopsy channel 34 should have a suitable wall thickness which can ensure both flexibility in bending directions and shape retainability. Furthermore, a jet outlet hole 36 is opened in the distal end face of the rigid tip end section 21.

Figure 3:
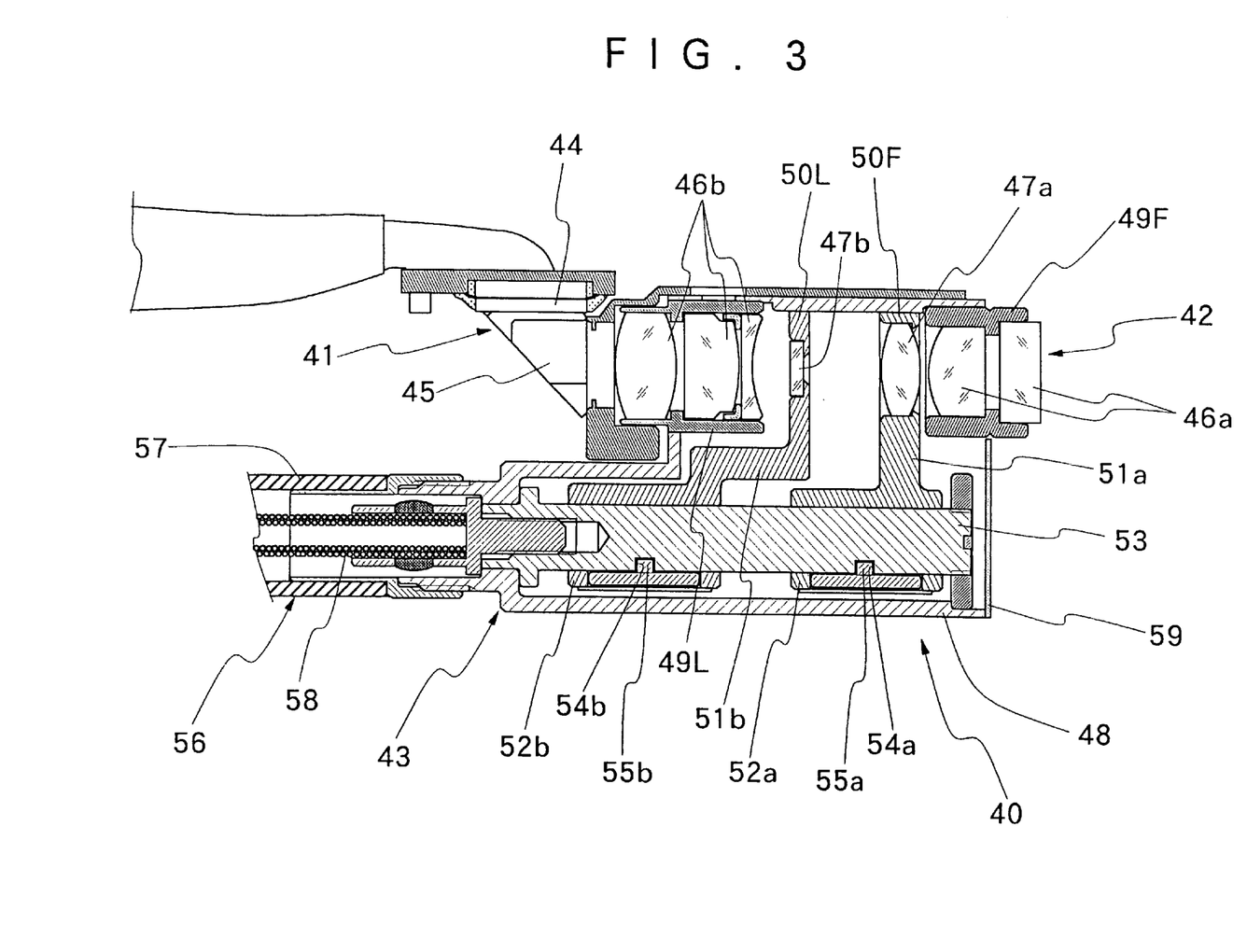
FIG. 3 is a schematic sectional view adopted for explanation of the arrangements of an optical image pickup assembly.

Shown in FIG. 3 is an endoscopic image pickup assembly which is fitted on the inner side of the observation window 30. The image pickup assembly is largely composed of an optical subassembly 40 and an image sensor means 41. The optical subassembly 40 includes an optical objective lens system 42 and its drive means 43. The image sensor means 41 includes a solid-state image sensor device 44 which is located at the focus of the objective lens system 42, and a prism 45 which functions to turn the light path of the objective lens system 42 through 90 degrees.

The optical objective lens system 42 is accommodated in a housing 48, including fixed lens groups 46a and 46b each consisting of at least one lens element, and movable lens groups 47a and 47b each consisting of one or a plural number of lens elements which are movable in the direction of optical axis. In this instance, the movable lens groups 47a and 48a are located between the fixed lens groups 46a and 46b and moved toward and away from each other, for example, for zooming actions.

The fixed lens groups 46a and 46b of the optical objective lens system 42 are mounted on fixed lens frames 49F and 49L, respectively. Provided between the fixed lens frames 49F and 49L are movable lens frames 50F and 50L on which the above-mentioned two movable lens groups 47a and 47b are mounted. These movable lens frames 50F and 50L is moved in the direction of optical axis through a cam mechanism. For this purpose, extended out radially outward from the movable lens frames 50F and 50L are arm members 51a and 51b which are provided with ring members 52a and 52b at the respective outer ends.

A cam shaft 53 is located in parallel relation with and at a distant position from the optical axis of the optical objective lens system 42. The cam shaft 53 is provided with a couple of cam grooves 54a and 54b on and around its circumferential surface. The ring members 52a and 52b are fitted on the cam shaft 54, and cam pins 55a and 55b which are provided on the par of the ring members 52a and 52b are engaged with the cam grooves 54a and 54b, respectively. Therefore, as the cam shaft 53 is turned in a forward or reverse direction, the cam pins 55a and 55b is slid or rolled along the cam grooves 54a and 54b, moving the movable lens frames 47a and 47b in the direction of optical axis.

The insertion instrument is provided with a control cable 56 as a rotational drive mens for turning the cam shaft 53. The control cable 56 has, within a flexible sleeve 57 which is connected to the housing 48, a flexible rotation transmission shaft 58 consists of tightly wound coils. The fore end of the flexible shaft 58 is connected to the cam shaft 53, while its rear or base end is connected to a rotational drive means such as an electric motor or the like. Therefore, upon rotating the base end of the flexible shaft about its axis, the rotation is transmitted to the cam shaft 53, causing the movable lens frames 50F and 50L toward or away from each other. In FIG. 3, indicated at 59 is a cap member which closes the fore end of the housing 48.

Figure 4:
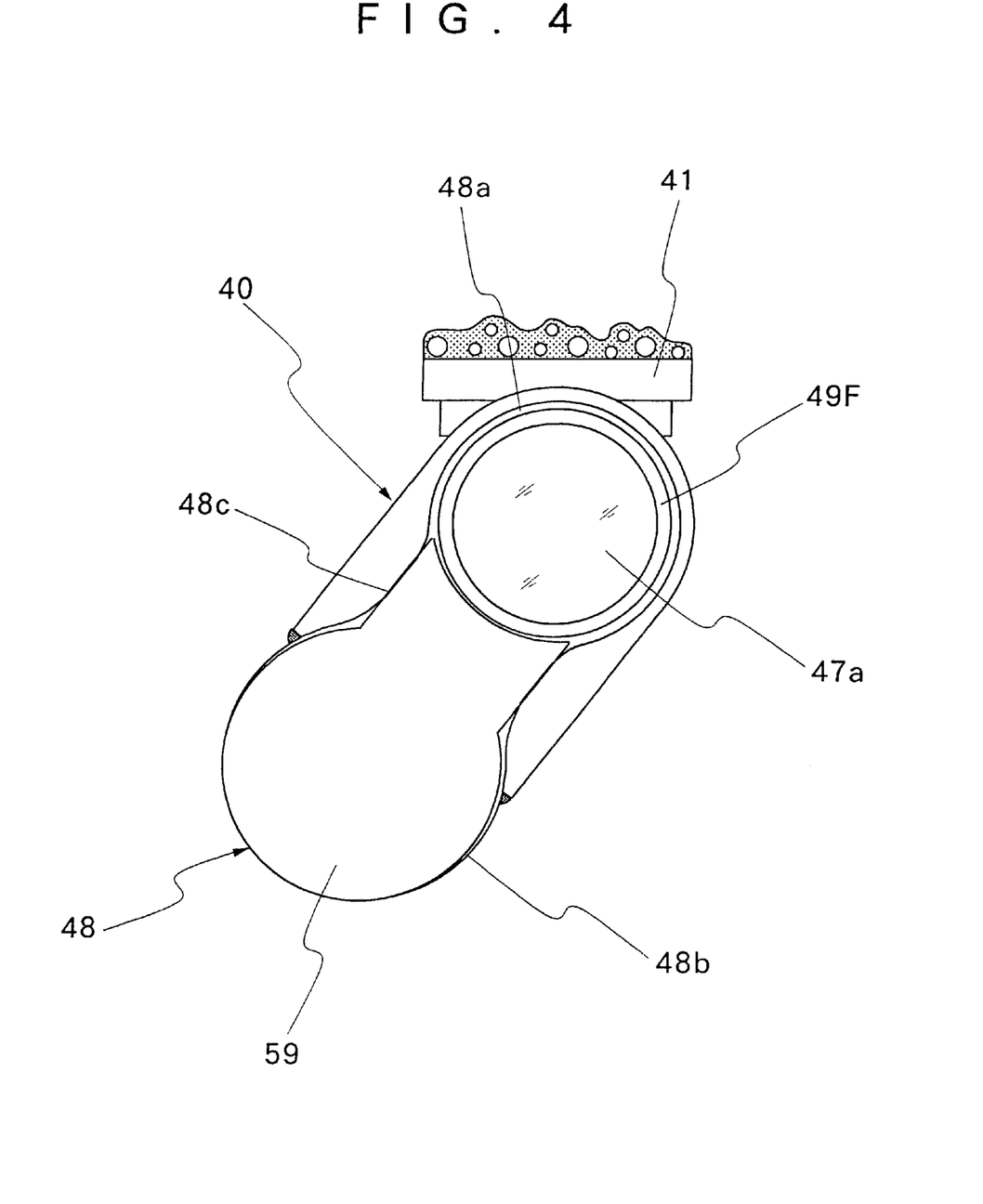
FIG. 4 is a right-hand side view of the image pickup assembly shown in FIG. 3.

The housing 48 constitutes a support structure for the optical subassembly 40. As shown in FIG. 4, the housing 48 is arranged to provide an optical system holder portion 48a in its upper portion and a cam member mount portion 48b in its lower portion. Both of the optical system holder portion 48a and the cam member mount portion 48b are circular in outer shape and are connected with each other by a narrower bridge portion 48c. The fixed lens frames 49F and 49L are fixedly retained in the optical system holder portion 48a, on the front and rear sides of a guide surface which guides the movable lens frames 50F and 50L in the direction of optical axis. On the other hand, the cam shaft 53 and associated parts are accommodated in the cam member mount portion. Further, the arms 51a and 51b of the movable lens frames 50F and 50L are located internally of the bridge portion 48c.

The control cable 56, as drive means for moving the movable lens frames 50F and 50L of the optical objective lens system 42 in the direction of optical axis, is extended in such a position as to avoid its interference with the objective lens system 42 and the image sensor means 41, thanks to the provision of the bridge portion 48c. However, the housing 48 and the control cable 56 are located on the proximal side of the tip end casing 24 and are not extended as far as the fore distal end face of the rigid tip end section 21. Accordingly, on the distal end face of the rigid tip end section 21, it is difficult to provide an opening such as the biopsy channel outlet opening 32 or the jet outlet opening 36 at a position on an axial extension line from the control cable 56.

On the other hand, fitted in an exposed state in the observation window 30 is a lens element of the optical objective lens system 42, more specifically, a foremost lens element of the fixed lens group 49 (or cover glass which simply has flat parallel surfaces and does not have any lens function). When the insertion instrument 20 is introduced into a body cavity of a patient, it is a usual experience that the exposed lens or glass surface of the observation window 30 is contaminated by deposition of body fluids or other contaminants. Therefore, the insertion instrument needs to be equipped with an observation window washing system to wash away such contaminants from the observation window 30. In the case of the preferred embodiment shown, the observation window washing system is arranged to spurt a wash fluid, i.e., a mixture of wash water and compressed air, toward the observation window 30 by the use of wash water and compressed air feed mechanisms and air/water feed valve which are substantially same as the counterparts in the above-described prior art.

Figure 5:
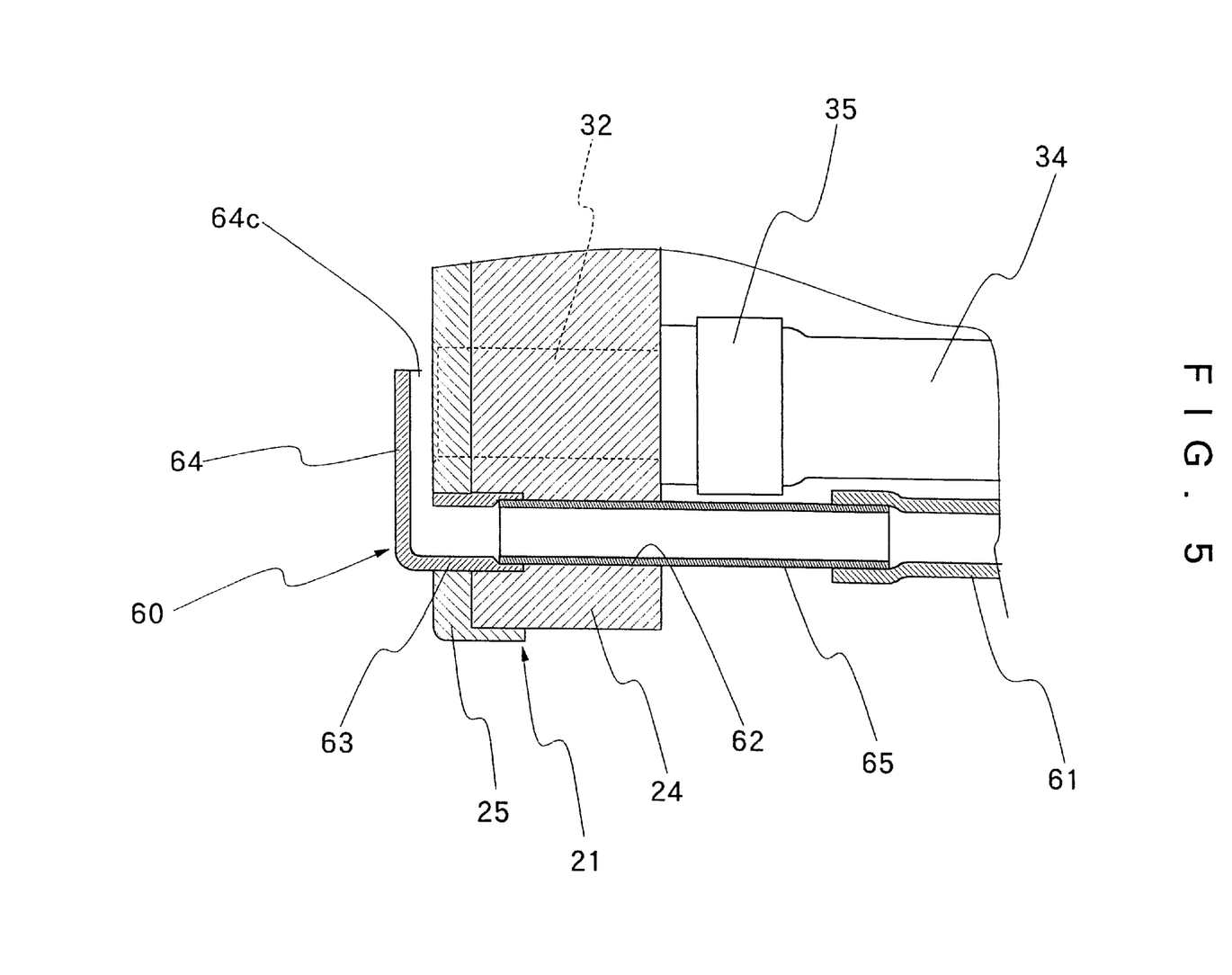
FIG. 5 is a schematic sectional view taken on line X—X of FIG. 2.

As shown in FIG. 5, in order to connect the junction pipe to the jet nozzle 60 which spurts out jets of the wash fluid toward the observation window 30, a fluid passage 62 is bored axially into the tip end casing 24. The jet nozzle 60, which should be arranged in such a way as to distribute a wash fluid over the entire surfaces of the observation window 30, includes a tubular body portion 63 to be connected to the axial fluid passage 62, and a jet spout passage portion 64 which is connected to the fore end of the tubular body portion 63 in such a way as to turn the flow direction of a wash fluid, which is supplied from the axial fluid passage 62, approximately through 90 degrees and spurt the wash fluid toward and along exposed outer lens surfaces of the observation window 30.

The axial fluid passage 62 is provided with a large diameter portion of a predetermined length from its front end, and the tubular body portion 63 of the jet nozzle 60 is fitted in this large diameter portion of the fluid passage 62. The tubular body portion 63, which serves as a fluid inlet passage of the jet nozzle, is fixedly fitted on a fore end portion of a connector pipe 62 which is also fitted in the fluid passage 62. Further, a junction pipe 61 in the form of a thick-walled flexible tube is fitted on a proximal end portion of the connector pipe 62. The jet spout passage portion 64 of the jet nozzle 60, which is adapted to spurt jets of the wash fluid in a switched direction, is formed in a tunnel-like shape and partly constituted by a surface portion of the insulating cap 25. If desired, the jet spout passage portion 64 can also be formed by deforming a tubular member into a flattened shape. In any case, outer wall surfaces of the jet passage 64 are projected from the insulating cap 25 to a certain extent.

As clear from FIG. 2, jets of wash fluid which are spurted out from the jet spout passage portion 64 of the jet nozzle 60 should cover at least the entire width of the observation window. Besides, the wash fluid which is spurted out from the jet spout passage portion 64 should be directed straight toward the center of the observation window 30. In this regard, it is to be noted that the jet spout passage portion 64 of the jet nozzle 60 is projected from the distal end face of the rigid tip end section 21. Further, a jet outlet opening 64c should be located at a certain distance from the observation window 30 because the view field through the observation window 30 can be restricted by the jet nozzle 60 in case the jet outlet hole 55 is located close to the observation window 30. Further, since the illumination windows 31 are located on the opposite sides of the observation window 30, light rays which are projected through the illumination windows 31 can be reflected off the wall surfaces of the jet nozzle 60 and cast on the observation window 30 as harmful light.

Taking the foregoing factors into consideration, in FIG. 2, the jet nozzle 60 has to be located on the distal end face of the rigid tip end section in the proximity of the position where the biopsy channel outlet 32 is opened. Besides, in spurting jets of the wash fluid from the jet spout passage portion 64 in a predetermined width A, arrangements should be made near center point of the observation window 30. Further, in order to spurt jets of wash fluid straight toward the observation window 30 from the jet outlet opening 64c which is located in a predetermined position relative to the observation window 30, the jet spout passage portion 64 should have a straight fluid passage of a sufficient length (or a forwardly diverging fluid passage) substantially in parallel relation with the center line B to spurt a jet of wash fluid in a straightforward direction toward the observation window 30. Namely, the jet spout passage portion 64 should have a straight fluid passage of a length L as a flow rectifying passage 64a. An inner end portion of the flow rectifying passage 64a is connected to a turn passage 64b which turns the flow direction of the wash fluid through approximately 90 degrees and in a radially diverting direction as will be described hereinafter. The inner end of the turn passage 64b is connected to the axial tubular portion or fluid inlet passage 63 which is in communication with the connector pipe 65, which is fitted in the fluid passage 62. The fore end of the flow rectifying passage 64a is terminated with the jet outlet opening 64c. The provision of the diverting turn passage 64b on the upstream side of the flow rectifying passage 64a of the jet nozzle 60 makes it possible to locate the fluid passage 62 in an arbitrary position on the tip end casing 24, almost irrespective of and not restricted by the actual position of the jet outlet opening 64c on the distal end face of the rigid tip end section 21.

Thus, in the case of an endoscopic insertion instrument of the sort as described above, there is a free space where no component part exists on the distal end face of the rigid tip end section 21 of the insertion instrument. That is, there is an unutilized free space at a position on an axial extension line from the housing 48 to which the control cable 56 is connected for driving the movable lens frames 47a and 47b of the optical objective lens system 42. However, the outlet 32 of the biopsy channel is opened at a position adjacent to that free space. Therefore, it is desirable to locate the jet spout passage portion 64 of the jet nozzle 60 in that free space. On the other hand, as shown particularly in FIG. 6, the junction pipe 61 which is connected to the fluid passage 62 is located in a space which exists between the biopsy channel 34 and the control cable 56.

Figure 6:
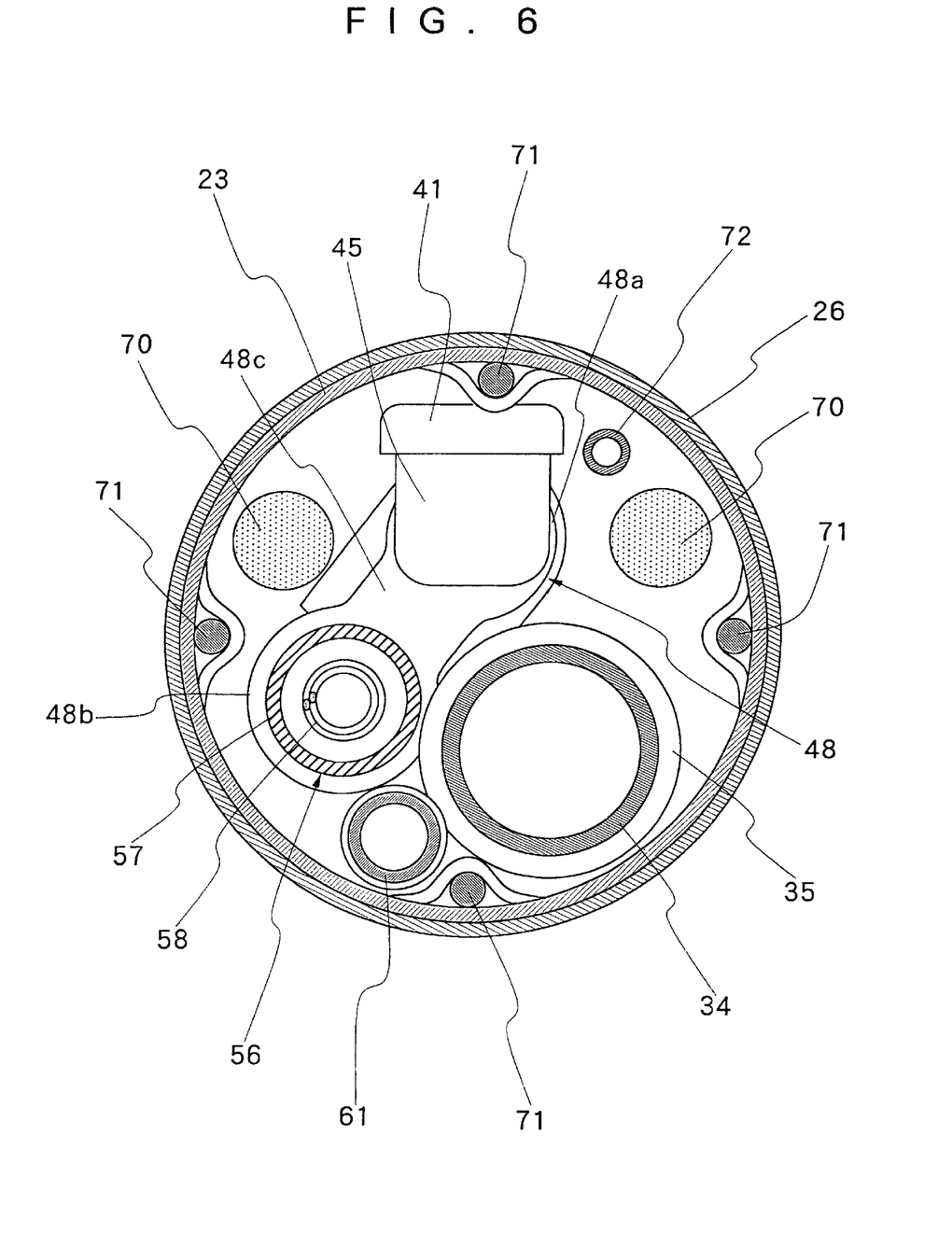
FIG. 6 is a schematic sectional view taken on line Y—Y of FIG. 1.

The biopsy channel 34 is connected to the proximal end face of the tip end casing 24 of the insertion instrument 20. Further, the control cable 56 is connected to the cam member mount portion 48b of the housing 48 of the optical assembly. Furthermore, the light guide 24 is also connected to the tip end casing 24. These component parts need to be threaded through the angle section 22, in addition to four remote-control operating wires 71 which are located in upper, lower, right and left positions within the angle section 22. Moreover, a tube 72 which communicates with the jet outlet hole 36 is a fitted in the angle section 22. Of all of these component parts which are fitted in or threaded through the angle section 22, the biopsy channel 34 and the control cable 56 are relatively large in diameter. In order to locate the control cable 56 in a position adjacent to the biopsy channel 34, the position of connection of the control cable 56 with the housing 48 is offset relative to the optical system holder portion 48a in a direction which perpendicularly intersects the longitudinal axis of the insertion instrument 20. This layout makes it possible to pass the junction pipe 61 through a small space which exists between the control cable 56 and the biopsy channel 34.

Accordingly, the junction pipe 61 is located in a position between the biopsy channel 34 and the cam member mount portion 48b, and, in the tip end casing 24, the fluid passage 62 is provided in a position on an axial extension line from the junction pipe 61. However, if the jet spout passage portion 64, with a width A sufficient for covering the entire surfaces of the observation window 30, is positioned parallel with a straight line drawn through a point D, on an extension line from a center axis of the junction pipe 61, and the center C of the observation window 30, the outlet opening 32 of the biopsy channel is blocked by walls of the jet spout passage portion 64 of the jet nozzle 60.

In order to avoid this problem, the turn passage 64b between the jet spout passage portion 64 and the axial tubular portion 63 of the jet nozzle 60 is gradually diverted in the circumferential direction from the center of the fluid passage 62 to let the jet spout passage portion 64 dodge the outlet opening 32 of the biopsy channel. Thus, the proximal end of the flow rectifying passage 64a in the jet spout passage portion 64 is located in an evasive position with respect to the outlet opening 32 of the biopsy channel, and its center line B is directed toward the center C or a near center point of the observation window 30. With these arrangements, jets of a wash fluid, which is a mixture of wash water and compressed air, can be spurted over the entire surfaces of the observation window in a desirable manner, permitting to wash away deposited contaminants and to purge water droplets therefrom in an extremely efficient manner and free of interference with other component parts on the distal end face of the rigid tip end section 21.

In short, the jet spout passage portion 64 of the jet nozzle 60, which is formed on the distal end face of the rigid tip end section 21, is constituted by a straight flow rectifying passage 64a and the diverting turn passage 64b. The provision of the diverting turn passage 64b makes it possible to locate the junction passage 61 and the ensuing fluid passage 62 in such a way as to utilize spaces which are available within the insertion instrument 20. Accordingly, the turn passage 64b is a sort of bypass passage which is radially diverted to a suitable degree and turned through an arbitrary angle to locate the jet spout passage portion 64 in an appropriate position on the distal end face of the rigid tip end section 21. Thus, above-described arrangements makes it possible to utilize internal spaces of the insertion instrument 20 in an extremely efficient manner, and to suppress dead spaces to a minimum for the purpose of making the insertion instrument 20 as small as possible in diameter.

As described above, the biopsy channel 34 is connected to the connector pipe through fitting engagement therewith, and an anchor ring 35 is fitted on a fore end portion of the biopsy channel 34 and thereby fixed in position. Therefore, this is the thickest part of the biopsy channel 34. The junction pipe 61 which is also in fitting engagement with the connector pipe 65 becomes thickest at this part. As clear from FIG. 5, that part of the biopsy channel 34 which is in fitting engagement with the connector pipe 56 is located immediately behind the proximal end face of the tip end casing 24, while that part of the junction pipe 61 which is in fitting engagement with the connector pipe 65 is located on the proximal side of the anchor ring 35 which is fitted on the biopsy channel 34 and within a rigid portion between the foremost angle ring 23 and a point of pivoting connection P of the foremost angle ring and an ensuing second angle ring. Thus, large diameter portions of the biopsy channel 34 and the junction pipe 61 are located in axially shifted positions from each other to make the most of the internal space of the insertion instrument 20.

Figure 7:
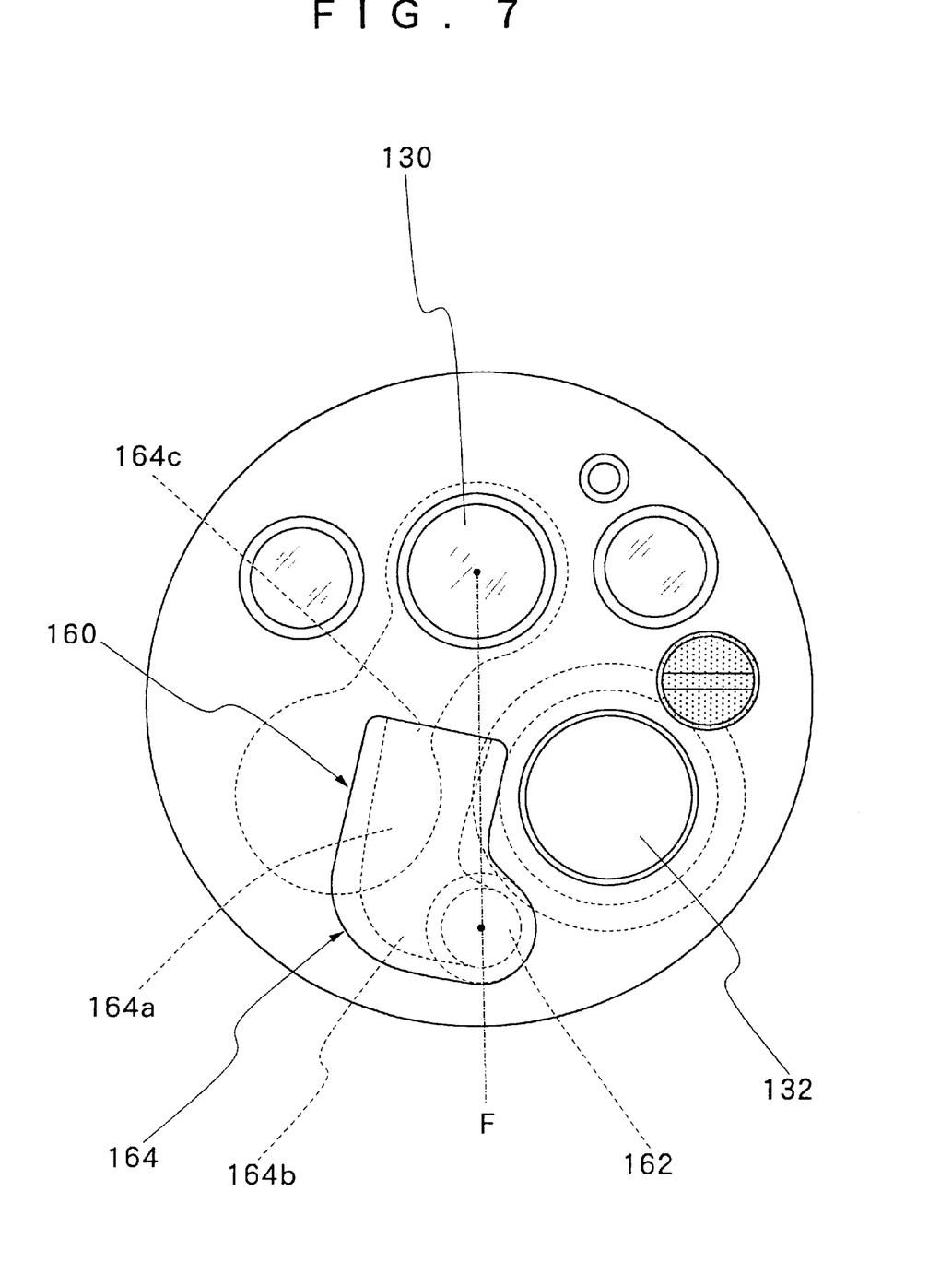
FIG. 7 is a view similar to FIG. 1 but showing another embodiment of the present invention.

Especially as shown in FIG. 7, even in a case where a fluid passage 162 to a jet nozzle 160 is located in such positional relations with an observation window 130 that a straight line which connects the centers of the fluid passage 162 and the observation window 130 passes a very close position to an outlet opening 132 of a biopsy channel, a jet spout passage portion 164 of a necessary length can be located in a diverted position clear of the biopsy channel outlet opening 132, by bending a diverting turn passage 164 approximately through 90 degrees or so in a direction away from the biopsy channel outlet opening 132. The jet outlet opening 164c at the fore distal end of the flow rectifying passage 164a in a diverted position is directed toward the observation window 130. By arranging the jet nozzle 160 in this manner, the flow direction of a wash fluid is turned along the turn passage 164b and spurted in a straightforward direction through the jet outlet opening 164c toward the observation window 30. Besides, the wash fluid can be spurted out through the jet outlet opening 164 substantially in a rectified state, permitting to wash and clean the observation window 30 completely in an efficient manner.

What is claimed is:

1. A jet nozzle connected to a distal end of an axial wash fluid passage in an endoscopic insertion instrument for spurting a wash fluid toward and on an observation window of an optical image pickup system fitted in a tip end section of said endoscopic insertion instrument, said jet nozzle comprising:

a wash fluid inlet passage provided in an axial bore formed axially through said tip end section in a direction of an optical axis of said optical image pickup system and opened in a circular end face of said tip end section; and a nozzle tip portion having a jet spout passage portion and a curved turn passage portion, wherein:

said jet spout passage portion is extending along a distal end face of said tip end section and provided with a flat flow rectifying passage; and said curved turn passage portion is connecting said wash fluid inlet passage and said jet spout passage portion to turn a flow passage of said wash fluid from said axial wash fluid passage to said jet spout passage portion and bent such that a center line of said flow rectifying passage is brought into alignment with a center of said observation window.

2. A jet nozzle as defined in claim 1, wherein said flat flow rectifying passage comprises one of a straight passage of a constant width and a straight passage with a width diverging toward an outlet opening thereof.

3. A jet nozzle as defined in claim 1, wherein said endoscopic insertion instrument comprises an optical objective lens system having movable lenses configured to be moved in the direction of the optical axis, said endoscopic insertion instrument further comprises a lens drive device configured to move the movable lenses, said axial wash fluid passage in said tip end section extends along an axial extension line of said lens drive device, and said curved turn passage is diverging from said wash fluid inlet passage toward said jet spout passage portion and configured to evade other component parts on said distal end face of said tip end section such that said jet spout passage portion directs jets of said wash fluid straight toward the center of said observation window free of interference with said other component parts.

4. A jet nozzle for spurting a wash fluid on an observation window of an optical image pickup system, comprising:

a tubular element having a wash fluid inlet passage portion and a nozzle tip portion, the wash fluid inlet passage portion being configured to be attached to a distal end of an axial wash fluid passage of an endoscopic insertion instrument of the optical image pickup system, the nozzle tip portion having a jet spout passage portion and a curved turn passage portion, wherein:

said jet spout passage portion is configured to extend along a distal end face of the endoscopic insertion instrument when attached to the distal end of the axial wash fluid passage of the endoscopic insertion instrument and has a flat flow rectifying passage; and said curved turn passage portion is connecting said wash fluid inlet passage and said jet spout passage portion and bent such that a center line of said flow rectifying passage is brought into alignment with a center of said observation window.

5. A jet nozzle as defined in claim 4, wherein said flat flow rectifying passage comprises one of a straight passage with a constant width and a straight passage with a width diverging toward an outlet opening thereof.

6. A jet nozzle as defined in claim 4, wherein said endoscopic insertion instrument comprises an optical objective lens system having movable lenses configured to be moved in the direction of the optical axis, said endoscopic insertion instrument further comprises a lens drive device configured to move the movable lenses, said axial wash fluid passage in said tip end section extends along an axial extension line of said lens drive device, and said curved turn passage is diverging from said wash fluid inlet passage toward said jet spout passage portion and configured to evade other component parts on said distal end face of said tip end section such that said jet spout passage portion directs jets of said wash fluid straight toward the center of said observation window free of interference with said other component parts.

* * * * *

UNITED STATES PATENT AND TRADEMARK OFFICE
CERTIFICATE OF CORRECTION

PATENT NO. : 6,595,915 B2
DATED : July 22, 2003
INVENTOR(S) : Akiba

It is certified that error appears in the above-identified patent and that said Letters Patent is hereby corrected as shown below:

<u>Title page,</u>
Item [30], Foreign Application Priority Data is incorrect. Item [30] should read:

-- [30]   Foreign Application Priority Data
Aug. 17, 2000  (JP) …………………..2000-247249 --

Signed and Sealed this

Fourth Day of November, 2003

JAMES E. ROGAN
*Director of the United States Patent and Trademark Office*